United States Patent [19]

Bull et al.

[11] 4,100,363
[45] Jul. 11, 1978

[54] 2-SUBSTITUTED ISOVALERIC ACID ESTER PESTICIDES

[75] Inventors: Michael J. Bull, Lower Halstow; Robert J. G. Searle, Sittingbourne, both of England

[73] Assignee: Shell Oil Company, Houston, Tex.

[21] Appl. No.: 787,684

[22] Filed: Apr. 14, 1977

Related U.S. Application Data

[62] Division of Ser. No. 687,483, May 18, 1976, Pat. No. 4,042,710.

[30] Foreign Application Priority Data

May 23, 1975 [GB] United Kingdom ............... 22662/75
Dec. 22, 1975 [GB] United Kingdom ............... 52342/75

[51] Int. Cl.² .................... C07C 69/24; A01N 9/24
[52] U.S. Cl. ............................ 560/255; 260/410.5; 424/305; 424/312
[58] Field of Search ................ 560/8, 130, 138, 221, 560/225, 255; 260/410.5

[56] References Cited

U.S. PATENT DOCUMENTS 3,996,244  12/1976  Fujimoto et al. .............. 560/221

FOREIGN PATENT DOCUMENTS 2,335,347  2/1974  Fed. Rep. of Germany.

OTHER PUBLICATIONS

Chemical Abstracts Item No. 120746w "Pesticidal Aromatic and Alicyclic Substituted Acetates," vol. 80, (1974).

*Primary Examiner*—James O. Thomas, Jr.
*Assistant Examiner*—L. Hendriksen

[57] ABSTRACT

Compounds of the formula $$\begin{array}{c} CH_3 \\ \phantom{CH_3}\diagdown \\ \phantom{CH_3}\phantom{\diagdown}CH-CH-\overset{R}{\underset{|}{C}}-\overset{O}{\underset{\|}{C}}-O\overset{X}{\underset{|}{CH}}-Y \\ \phantom{CH_3}\diagup \\ CH_3 \end{array}$$

wherein R is alkenyl, aralkyl or alkyl; X is H, CN, thioamide, or alkynyl; and Y is phenoxyphenyl or phthalimido, are useful as pesticides.

3 Claims, No Drawings

2-SUBSTITUTED ISOVALERIC ACID ESTER PESTICIDES

This is a division of application Ser. No. 687,483, filed May 18, 1976, now U.S. Pat. No. 4,042,710.

This invention relates to certain new substituted isovalerates, their use as pesticides and to pesticidal compositions containing these new isovalerates.

SUMMARY OF THE INVENTION

The present invention is directed to 2-substituted isovalerates of the formula I

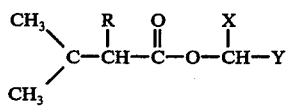

wherein R represents an alkyl or alkenyl group or an optionally substituted aralkyl group; X represents a hydrogen atom, or a cyano, thioamide or alkynyl group; and Y represents a phthalimido or phenoxyphenyl group.

Preferred compounds are those 2-substituted isovalerates of formula I wherein R represents an alkyl group of 1 to 16 carbon atoms, which may be branched, such as an isopropyl, isobutyl or isoamyl group, or may be straight chain, such as methyl, ethyl, n-propyl, n-butyl, n-hexyl, n-octyl or n-dodecyl group, an alkenyl group of up to 6 carbon atoms, such as allyl, butenyl or pentenyl, or a benzyl group optionally substituted by one or more halogen atoms of atomic number of 9 to 35, inclusive, such as chlorine or by alkyl of 1 to 6 carbon atoms, such as methyl; X represents a hydrogen atom, a cyano group, a thioamide group or alkynyl of 2 to 6 carbon atoms, such as ethynyl; and Y represents a phenoxyphenyl or phthalimido group, especially a 3-phenoxyphenyl group.

Preferred because of their pesticidal properties are those compounds of formula I wherein R represents a branched chain alkyl group of 1 to 16 carbon atoms or an alkenyl group of 2 to 6 carbon atoms or a benzyl group optionally substituted by one or more halogen atoms or alkyl groups and Y represents a phenoxyphenyl group.

A particularly preferred subclass comprises those compounds of formula I wherein R represents a branched chain alkyl group of 1 to 6 carbon atoms, an optionally alkyl substituted-allyl group or a benzyl group optionally substituted by halogen, especially chlorine or by an alkyl group of 1 to 6 carbon atoms, especially methyl.

In general the compounds of formula I which are preferred are those where X represents a cyano group.

The 2-substituted isovalerates of the invention may be prepared by a process which comprises reacting a compound of formula:

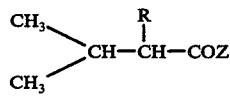

with a compound of formula:

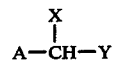

wherein one of the groups Z and A represents a halogen, suitably chlorine or bromine, atom and the other represents a hydroxy group; the other substituents having the meanings defined in formula I above. The reaction is conveniently carried out in the presence of a hydrogen halide acceptor, suitably a carbonate such as potassium carbonate, or a tertiary amine such as triethylamine, and in an organic solvent, such as toluene or acetone.

The compound of formula II may be prepared by appropriate adaptation of known synthesis procedures. Convenient routes include the reaction of a 2-propyl halide (e.g. bromide) with a malonate or cyanoacetate, followed by reaction with the halide R—Hal and decarboxylation.

The isovalerates of the invention are of interest as pesticides, particularly as tickicides, insecticides and acaricides for agricultural and domestic outlets. The invention therefore includes within its scope pesticidal compositions comprising a carrier and/or a surface-active agent together with, as active ingredient, an isovalerate of formula I. Likewise the invention also includes a method of combating tick, insect and/or acarid pests at a locus which comprises applying to the locus a pesticidally effective amount of an isovalerate derivative or composition of the invention. The compounds also have relatively low toxicities to fish and mammals.

The term 'carrier' as used herein means a solid or fluid material, which may be inorganic or organic and of synthetic or natural origin, with which the active compound is mixed or formulated to facilitate its application to the plant, seed, soil or other object to be treated, or its storage, transport or handling. The carrier may be a solid or a fluid. Any of the materials usually applied in formulating pesticides may be used as the carrier.

Suitable solid carriers are natural and synthetic clays and silicates, for example natural silicas such as diatomacious earths; magnesium silicates, for example, talcs; magnesium aluminium silicates, for example, attapulgites and vermiculites; aluminium silicates, for example, kaolinites, montmorillinites and micas; calcium carbonates; calcium sulphate; synthetic hydrated silicon oxides and synthetic calcium or aluminium silicates; elements such as for example, carbon and sulphur; natural and synthetic resins such as, for example coumarone resins, polyvinyl chloride and styrene polymers and copolymers; solid polychlorophenols; bitumen; waxes such as for example, beeswax, paraffin wax, and chlorinated mineral waxes; and solid fertilisers, for example superphosphates.

Examples of suitable fluid carriers are water, alcohols, such as for example, isopropanol, glycols; ketones such as for example, acetone, methyl ethyl ketone, methyl isobutyl ketone and cyclohexanone; ethers; aromatic hydrocarbons such as for example, benzene, toluene and xylene; petroleum fractions such as for example, kerosine, light mineral oils; chlorinated hydrocarbons, such as for example, carbon tetrachloride, perchloroethylene, trichloroethane, including liquefied normally vaporous gaseous compounds. Mixtures of different liquids are often suitable.

The surface-active agent may be an emulsifying agent or a dispersing agent or a wetting agent; it may be non-ionic or ionic. Any of the surface-active agents usually applied in formulating herbicides, fungicides, or insecticides may be used. Examples of suitable surface-active agents are the sodium or calcium salts of polyacrylic acids and lignin sulphonic acids; the condensation products of fatty acids or aliphatic amines or amides containing at least 12 carbon atoms in the molecule with ethylene oxide and/or propylene oxide; fatty acid esters of glycerol, sorbitan, sucrose or pentaerythritol; condensates of these with ethylene oxide and/or propylene oxide; condensation products of fatty alcohols or allyl phenols for example p-octylphenol or p-octylcresol, with ethylene oxide and/or propylene oxide; sulphates or sulphonates of these condensation products; alkali or akaline earth metal salts, preferably sodium salts, of sulphuric or sulphonic acid esters containing at least 10 carbon atoms in the molecule, for example, sodium lauryl sulphate, sodium secondary alkyl sulphates, sodium salts of sulphonated castor oil, and sodium alkylaryl sulphonates such as sodium didecylbenzene sulphonate; and polymers of ethylene oxide and copolymers of ethylene oxide and propylene oxide.

The compositions of the invention may be formulated as wettable powders, dusts, granules, solutions, emulsifiable concentrates, emulsions, suspension concentrates and aerosols and will generally contain 0.5 to 95% w, preferably 0.5 to 75% w, of toxicant. Wettable powders are usually compounded to contain 25, 50 or 755 % of toxicant and usually contain, in addition to solid carrier, 3–10% w of a dispersing agent and, where necessary, 0–10% w of stabliser(s) and/or other additives such as penetrants or stickers. Dusts are usually formulated as a dust concentrate having a similar composition to that of a wettable powder but without a dispersant, and are diluted in the field with further solid carrier to give a composition usually containing ½–10% w of toxicant. Granules are usually prepared to have a size between 10 and 100 BS mesh (1.676–0.152 mm), and may be manufactured by agglomeration or impregnation techniques. Generally, granules will contain ½–25% w toxicant and 0–10% w of additives such as stabilisers, slow release modifiers and binding agents. Emulsifiable concentrates usually contain, in addition to the solvent and, when necessary, co-solvent, 10–50% w/v toxicant, 2–20% w/v emulsifiers and 0–20% w/v of appropriate additives such as stabilisers, penetrants and corrosion inhibitors. Suspension concentrates are compounded so as to obtain a stable, non-sedimenting, flowable product and usually contain 10–75% w toxicant, 0.5–15% w of dispersing agents, 0.1–10% w of suspending agents such as protective colloids and thixotropic agents, 0–10% w of appropriate additives such as defoamers, corrosion inhibitors, stabilisers, penetrants and stickers, and as carrier, water or an organic liquid in which the toxicant is substantially insoluble; certain organic salts may be dissolved in the carrier to assist in preventing sedimentation or as antifreeze agents for water.

Aqueous dispersions and emulsions, for example, compositions obtained by diluting a wettable powder or a concentrate according to the invention with water, also lie within the scope of the present invention. The said emulsions may be of the water-in-soil or of the oil-in-water type, and may have a thick 'mayonnaise'-like consistency.

The compositions of the invention may also contain other ingredients, for example, other compounds possessing pesticidal, for example insecticidal, acaricidal, herbicidal or fungicidal properties.

The invention is further illustrated in the following Examples:

EXAMPLE I 2-isopropyl 4-methylpent-4 enoic acid, alpha-cyano-3 phenoxybenzyl ester (a) Preparation of 2-isopropyl-4-methylpent-4-enoic acid Diethylmalonate (80.0g) in ethyl alcohol (50ml) was added to a solution of sodium ethoxide (prepared from sodium metal (13.0g) and absolute alcohol (400ml)) over 15 minutes whilst gently refluxing the mixture. After stirring under reflux for 1 hour a solution of 2-bromopropane (74.5g) in alcohol (50ml) was added over 1 hour and the mixture stirred under reflux overnight. The reaction mixture was cooled in ice and inorganic material removed by filtration and the filtrate concentrated. Water was added to the concentrate which was extracted with ether, the ethereal extracts washed with 2N sodium hydroxide solution (X2) and dried over magnesium sulphate. Removal of solvent gave an almost colourless liquid which was further purified by distillation to give diethyl isopropylmalonate b.p. 62°–65° C/0.7 mm Hg.

A solution of diethyl isopropylmalonate (8.1g) in 25 ml of a 25% solution of HMPT (hexamethylphosphorus triamide) in toluene was added dropwise over 15 minutes to a suspension of sodium hydride (50mM) in 25% HMPT/toluene (50ml) at room temperature. The mixture was then stirred at 60° C for ½ hour, cooled to 25° C and methallyl chloride (4.0g) in 25% HMPT/toluene was added over 10 minutes. The mixture was stirred at 80°–85° C overnight, cooled to room temperature and poured onto a mixture of ice/hydrochloric acid. The product was extracted with ether, the ethereal extracts washed with water, followed by 2N sodium hydroxide and then water, and dried over magnesium sulphate. Removal of solvent gave diethyl isopropyl-2-methylprop-2-enylmalonate as a pale yellow liquid. R.I. $n_D^{21}$ 1.4467.

A mixture of diethyl isopropyl-2-methylprop-2-enylmalonate (8.7g), potassium hydroxide (20g), water (20ml) and methylated spirits (10ml) was stirred under reflux overnight. The mixture was diluted with water (200ml) and washed with ether (X3). The aqueous portion was acidified with conc. hydrochloric acid and the acid product extracted with ether (X3), washed with water and dried over magnesium sulphate. Removal of solvent gave the disubstituted malonic acid (5.3g) which was then decarboxylated at 200° C for 1½ hours under nitrogen. the crude product was dissolved in ether, washed with water and the ethereal extract treated with 2N sodium hydroxide (X2) and washed with ether. The aqueous phase was acidified with conc. hydrochloric acid and the product extracted with ether (X2) washed with water and dried over magnesium sulphate. Removal of solvent gave the required 2-isopropyl-4-methylpent-4-enoic acid. R.I. $n_D^{21} = 1.4459$.

Analysis: Calculated for $C_9H_{16}O_2$: C 69.2; H 10.3. Found: C 69.4; H 10.7.

(b) Esterification of 2-isopropyl-4-methylpent-4-enoic acid

A mixture of 2-isopropyl-4-methylpent-4-enoic acid (1.0g), alphacyano-3-phenoxybenzyl bromide (1.9g) and potassium carbonate (1.0g) in anhydrous acetone (40ml) was stirred at room temperature for 4 hours. Water was added to the reaction mixture and the product extracted with ether, the ethereal extracts washed with water (X2) and dried over magnesium sulphate. Evaporation of the solvent gave a crude product which was purified by chromatography on silica gel using 3% acetone in 60°–80° C petroleum ether as eluent to give the desired ester. R.I. $n_D^{20}$ 1.5343.

Analysis: Calculated for $C_{23}H_{25}NO_3$: C 76.1; H 6.9; N 3.9%. Found: C 76.0; H 7.0; N 3.6%.

EXAMPLE 2

Preparation of 2-isopropylpentanoic acid, alpha-cyano-3-phenoxy benzyl ester (a) Preparation of 2-isopropylpentanoic acid Diethylmalonate (80.0g) in ethyl alcohol (50ml) was added to a solution of sodium ethoxide (prepared from sodium metal (13.0g) and absolute alcohol (400ml)) over 15 minutes whilst gently refluxing the mixture. After stirring under reflux for 1 hour a solution of 2-bromopropane (74.5g) in alcohol (50ml) was added over 1 hour and the mixture stirred under reflux overnight. The reaction mixture was cooled in ice and inorganic material removed by filtration and the filtrate concentrated. Water was added to the concentrate which was extracted with ether, the ethereal extracts washed with 2N sodium hydroxide solution (X2) and dried over magnesium sulphate. Removal of solvent gave an almost colourless liquid which was further purified by distillation to give diethyl isopropylmalonate b.p. 62°–65° C/0.7 mm Hg.

A solution of diethylisopropylmalonate (10.1g) in 15 ml of a 25% solution of HMPT (hexamethylphosphorus triamide) in toluene was added dropwise over 15 minutes to a suspension of sodium hydride (70mM) in 25% HMPT/toluene (15ml) at 50°–70° C. N-propyl iodide (17.0g) was then added over 30 minutes at 70°–100° C and the mixture stirred at 120°–130° C for 1½ hours. After cooling, methylated spirits (10ml) was added and the mixture poured onto a mixture of ice/hydrochloric acid. The product was extracted with ether, the ethereal extracts washed with sodium bicarbonate (X2), then water and dried over anhydrous magnesium sulphate. Removal of the solvent gave diethyl 2-isopropyl-2-propylmalonate as a yellow liquid b.p. 92°–94°/1 mm Hg. 87% yield.

Analysis: Calculated for $C_{13}H_{24}O_4$: C 63.9; H 9.8% Found: C 63.1; H 10.1%.

A mixture of diethyl 2-isopropyl-2-propylmalonate (10.0g), potassium hydroxide (20g), water (20ml) and methylated spirits (10ml) was stirred under reflux overnight. After dilution with water (200ml) the mixture was washed with ether (X2). The aqueous portion was acidified with conc. hydrochloric acid and the acid product extracted with ether (X3), washed with water and dried over anhydrous magnesium sulphate. Removal of solvent gave the disubstituted malonic acid which was then decarboxylated by stirring overnight in gently reluxing xylene (60ml). The reaction product was cooled in an ice bath, diluted with ether, washed with water (X2) and the ethereal extract treated with 2M sodium hydroxide (X2). The basic aqueous phase was acidified with conc. hydrochloric acid and the product extracted with ether (X2), washed with water and dried over anhydrous magnesium sulphate. Removal of solvent gave the required 2-isopropylpentanoic acid R.I. $n_D^{21}$ 1.4263. Yield 85%.

Analysis: Calculated for $C_8H_{16}O_2$: C 66.7; H 11.1%. Found: C 66.4; H 11.0%.

(b) Esterification of 2-isopropylpentanoic acid

A mixture of 2-isopropylpentanoic acid (0.8g), alpha-cyano-3-phenoxybenzyl bromide (1.45g) and potassium carbonate (0.8g) in anhydrous acetone (30ml) was stirred at room temperature for 2 hours. Water was added to the reaction mixture and the product extracted with ether, the ethereal extracts washed with sodium bicarbonate (X3) and dried over anhydrous magnesium sulphate. Evaporation of the solvent gave a crude product which was purified by chromatography on silica gel using 3% acetone in 60°–80° C petroleum ether as eluent to give the desired ester. R.I. $n_D^{21}$ 1.5237.

Analysis: Calculated for $C_{22}H_{25}NO_3$: C 75.2; H 7.1; N 4.0. Found: C 75.4; H 7.4; N 3.6.

EXAMPLE 3

Preparation of 2-allyl isovaleric acid, alpha thioamido-3-phenoxy benzyl ester 2-allyl isovaleric acid, alpha-cyano-3-phenoxy benzyl ester (prepared in a manner analogous to that of Example 3; 3.5g), dimethyl formamide (30ml), and triethanolamine (4ml) were stirred together at room temperature, the apparatus purged with dry nitrogen gas for 15 minutes, and a slow stream of hydrogen sulphide gas then bubbled through the mixture for 3 hours at room temperature. Nitrogen gas was then passed through the mixture to remove excess hydrogen sulphide, leaving a clear, light green solution. This product was poured into water, extracted twice with diethyl ether, washed with water (X6) and dried over anhydrous magnesium sulphate. Removal of the ether solvent gave a crude product as a yellow oil, which was purified by chromatography on silica gel using methylene dichloride as eluant to yield the desired product. R.I. $n_D^{23}$ = 1.5843.

Analysis: Calculated for $C_{22}H_{25}NSO_3$: C 69.0; H 6.5; N 3.6; S 8.3%. Found: C 68.5; H 6.2; N 3.5; S 8.2%.

EXAMPLE 4–30

Following procedures similar to those described in Example 1–3, further compounds according to the invention were prepared. The physical characteristics and analyses are given in Table 1 in which the compounds are identified by reference to the substituents in formula I.

EXAMPLE 31

Pesticidal activity

The insecticidal, acaricidal and tickicidal activity of the compounds according to the present invention was tested as follows:

I. A 1.0% by weight solution in acetone of the compound to be tested was prepared, and taken up in a micrometer syringe. Two to 3-day old adult female house flies (*Musca domestica*) was anaesthetized with carbon dioxide, and 1 μl drop of the test solution was brushed off on the ventral abdomen of each, 20 flies being treated. The treated flies were held for 24 hours in glass jars, each containing a little granulated sugar as food for the flies, and the percentage of dead and moribund individuals was then recorded.

TABLE I

| Ex. No. | R | X | Y | R.I. or m.p. | Analysis | |
|---|---|---|---|---|---|---|
| 4 | isopropyl | —CN | 3-phenoxyphenyl | $n_D^{23}$ 1.5320 | Calculated for $C_{22}H_{25}NO_3$<br>Found | C 75.2 ; 7.1 ; N 4.0%<br>C 74.1 ; H 6.8 ; N 3.7% |
| 5 | isopropyl | H | " | $n_D^{23}$ 1.5260 | Calculated for $C_{21}H_{26}O_3$<br>Found | C 77.2 ; H 8.0%<br>C 77.7 ; H 8.2% |
| 6 | p-chlorobenzyl | —CN | " | $n_D^{20}$ 1.5360 | Calculated for $C_{26}H_{24}NO_3Cl$<br>Found | C 72.0 ; H 5.5 ; N 3.2%<br>C 70.8 ; H 5.6 ; N 2.9% |
| 7 | m-chlorobenzyl | —CN | " | $n_D^{20}$ 1.5620 | Calculated for $C_{26}H_{24}NO_3Cl$<br>Found | C 72.0 ; H 5.5 ; N 3.2%<br>C 71.9 ; H 5.3 ; N 3.0% |
| 8 | 2,3-dimethylbenzyl | —CN | " | $n_D^{20}$ 1.5582 | Calculated for $C_{28}H_{29}NO_3$<br>Found | C 78.6 ; H 6.8 ; N 3.3%<br>C 78.6; H 6.8 ; N 3.1% |
| 9 | " | H | " | $n_D^{20}$ 1.5601 | Calculated for $C_{27}H_{30}O_3$<br>Found | C 80.6; H 7.5%<br>C 80.9 ; H 7.6% |
| 10 | allyl | CN | " | $n_D^{20}$ 1.5345 | Calculated for $C_{22}H_{23}NO_3$<br>Found | C 75.6 ; H 6.6 ; N 4.0%<br>C 76.0 ; H 6.9 ; N 3.9% |
| 11 | 3-methyl allyl | CN | " | $n_D^{21}$ 1.5358 | Calculated for $C_{23}H_{25}NO_3$<br>Found | C 76.1 ; H 6.9 ; N 3.9%<br>C 76.2 ; H 7.0 ; N 3.7% |
| 12 | 3,3-dimethyl allyl | CN | " | $n_D^{19}$ 1.5331 | Calculated for $C_{24}H_{27}NO_3$<br>Found | C 76.4 ; H 7.2 ; N 3.7%<br>C 76.7 ; N 7.2 ; N 3.5% |
| 13 | n-butyl | —CN | " | $n_D^{21}$ 1.5232 | Calculated for $C_{23}H_{27}NO_3$<br>Found | C 75.6 ; H 7.4 ; N 3.8%<br>C 75.3 ; H 7.3 ; N 3.7% |
| 14 | ethyl | —CN | " | $n_D^{21}$ 1.5302 | Calculated for $C_{21}H_{23}NO_3$<br>Found | C 74.7 ; H 6.8 ; N 4.15%<br>C 75.11 ; H 6.9 ; N 3.9% |
| 15 | n-hexyl | —CN | " | $n_D^{21}$ 1.5189 | Calculated for $C_{25}H_{31}NO_3$<br>Found | C 76.3 ; H 7.9 ; N 3.55%<br>C 76.0 ; H 8.1 ; N 3.4% |
| 16 | n-propyl | H | " | $n_D^{22}$ 1.5285 | Calculated for $C_{21}H_{26}O_3$<br>Found | C 77.3 ; H 8.0%<br>C 77.4 ; H 8.0% |
| 17 | n-butyl | —C≡CH | " | $n_D^{18}$ 1.5312 | Calculated for $C_{24}H_{30}O_3$<br>Found | C 79.1 ; H 7.7%<br>C 79.0 ; H 7.9% |
| 18 | n-dodecyl | —CN | 3-phenoxyphenyl | $n_D^{20}$ 1.5090 | Calculated for $C_{31}H_{43}NO_3$<br>Found | C 78.0 ; H 9.0 ; N 2.9%<br>C 78.3; H 9.5 ; N 2.7% |
| 19 | n-octyl | —CN | " | $n_D^{22}$ 1.5154 | Calculated for $C_{27}H_{35}NO_3$<br>Found | C 77.0 ; H 8.3 ; N 3.3%<br>C 77.3 ; H 8.5 ; N 3.0% |
| 20 | methyl | —CN | " | $n_D^{22}$ 1.5345 | Calculated for $C_{20}H_{21}NO_3$<br>Found | C 74.3 ; H 6.5 ; N 4.3<br>C 74.1 ; H 6.7 ; N 4.0% |
| 21 | 3,3-dimethyl allyl | —C≡CH | " | $n_D^{22}$ 1.5340 | Calculated for $C_{25}H_{28}O_3$<br>Found | C 79.8 ; H 7.5%<br>C 79.8 ; H 7.5% |
| 22 | isoamyl | CN | 3-phenoxyphenyl | $n_D^{22}$ 1.5194 | Calculated for $C_{24}H_{29}NO_3$<br>Found | C 76.0 ; H 7.6 ; N 3.7%<br>C 75.6 ; H 7.6; N 3.4% |
| 23 | isobutyl | CN | " | $n_D^{24}$ 1.5220 | Calculated for $C_{23}H_{27}NO_3$<br>Found | C 75.6 ; H 7.4 ; N 3.8%<br>C 75.6 ; H 7.5 ; N 3.6% |
| 24 | pentenyl-1 | CN | " | $n_D^{22}$ 1.5298 | Calculated for $C_{24}H_{27}NO_3$<br>Found | C 76.4 ; H 7.2 ; N 3.7%<br>C 76.1 ; H 7.3 ; N 3.3% |
| 25 | 3,3-dimethyl allyl | H | phthalimido | $n_D^{22}$ 1.5026 | Calculated for $C_{19}H_{27}NO_4$<br>Found | C 68.4 ; H 8.1 ; N 4.2%<br>C 68.2 ; H 8.1 ; N 3.9% |
| 26 | allyl | H | " | $n_D^{23}$ 1.5316 | Calculated for $C_{17}H_{19}NO_4$<br>Found | C 67.8 ; H 6.3 ; N 4.7%<br>C 68.0 ; H 6.3 ; N 4.8% |
| 27 | n-hexyl | H | " | $n_D^{18}$ 1.5091 | Calculated for $C_{20}H_{31}NO_4$<br>Found | C 68.7 ; H 8.9 ; N 4.0%<br>C 68.3 ; H 9.2 ; N 3.7% |
| 28 | $C_2H_5$ | H | " | m. pt. 48–9° C | Calculated for $C_{16}H_{19}NO_4$<br>Found | C 66.5 ; H 6.6 ; N 4.8%<br>C 66.2 ; H 6.6 ; N 4.8% |
| 29 | $CH_3OCH_2$ | CN | " | $n_D^{18}$ 1.5351 | Calculated for $C_{21}H_{23}NO_4$<br>Found | C 71.4 ; H 6.5 ; N 4.0%<br>C 71.8 ; H 6.6 ; N 3.8% |
| 30 | $(CH_3)_3C—CH_2—CH_2$ | CN | 3-phenoxyphenyl | $n_D^{21}$ 1.5179 | Calculated for $C_{25}H_{31}NO_3$<br>Found | C 76.4 ; H 7.9 ; N 3.5%<br>C 76.1 ; H 8.1 ; N 3.3% |

II. The compounds were formulated as solutions or suspensions in water containing 20% by weight of acetone and 0.05% by weight of Triton X 100 as wetting agent. The formulations contained 0.7% by weight of the compound to be tested. Turnip and broad bean plants, trimmed to one leaf each, were sprayed on the under-surface of the leaf with the above formulation. Spraying with a spraying machine delivering 450 liters per hectare, the plants passing under the spray on a moving belt. Ten adult 1-2 week-old mustard beetles (*Phaedon cochleariae*) were placed on the spraying leaf of each turnip plant and ten apterous (6-day-old) vetch aphids (*Megoura viciae*) were placed on the sprayed leaf of each broad bean plant. The plants were then enclosed in glass cylinders fitted at one end with a muslin cap. Mortality counts were made after 24 hours.

III. In tests against glass house spider mites (*Tetranychus urticae*), leaf discs cut from French bean plants were sprayed in the manner described under II. 1 hour after spraying, the discs were inoculated with 10 adult mites. Mortality counts were made 24 hours after inoculation.

IV. The compounds were formulated as solutions or fine suspensions in water containing 20% by weight of acetone and 0.05% by weight of Triton D 100 as wetting agent. The formulations contained 0.6% by weight of the compound to be tested. Pairs of leaves are removed from broad bean plants and placed on filter paper inside plastic petri dishes. Immediately prior to testing 10 larvae of the Egyptian cotton leafworm (*Spodoptera littoralis*) are transferred onto the leaves and allowed to settle down. Larvae and leaves are sprayed together using a spraying machine delivering 340 liters/hectare. operated under the conveyor belt principle. After spraying the larvae are covered with a petri dish lid. After 24 hours, the percentage of dead and moribund larvae was recorded.

V. The compounds were formulated as solutions or fine suspensions in acetone containing 10% by weight of polyethylene glycol having an average molecular weight of 400. The formulations contained 0.1% by weight of the compound to be tested. 1 ml of the above-mentioned solution is applied evenly to a filter paper situated inside a petri dish. After the paper is sufficiently dry it is folded in half and partly crimped along the outer edge to form a packet. About 80–100 larval ticks (*Boophilus microplus*) are transformed into the packet which is then sealed completely. The packets are placed inside an incubator, maintained at 27° C and 80% relative humidity, before assessing mortality 24 hours later.

The results of these tests are shown in Table II in which the test species are identified by the initials noted above, and A denotes complete kill, B some kill and C no kill of the test species.

TABLE II

| Compound of Example | Pesticidal Activity | | | | | |
| --- | --- | --- | --- | --- | --- | --- |
| | M.d. | P.c. | S.l. | M.v. | T.u. | B.m. |
| 1 | A | B | A | A | B | A |
| 2 | A | A | A | A | B | A |
| 3 | C | C | C | A | B | B |
| 4 | A | B | B | A | B | A |
| 6 | A | B | B | A | C | B |
| 8 | C | C | C | B | B | A |
| 9 | C | C | A | C | B | C |
| 10 | A | A | A | A | A | A |
| 11 | A | B | C | A | B | A |
| 13 | A | B | C | A | A | A |
| 14 | A | A | A | A | B | A |
| 15 | A | B | A | A | B | A |
| 16 | C | B | C | A | B | A |
| 17 | A | B | A | A | B | A |
| 19 | C | B | C | A | B | A |
| 21 | B | A | C | A | C | B |
| 22 | A | C | A | A | A | A |
| 23 | A | C | A | — | A | — |
| 24 | A | B | A | B | C | A |

TABLE II-continued

| Compound of Example | Pesticidal Activity | | | | | |
| --- | --- | --- | --- | --- | --- | --- |
| | M.d. | P.c. | S.l. | M.v. | T.u. | B.m. |
| 27 | C | B | C | A | B | B |

What we claim is:
1. A compound of the formula

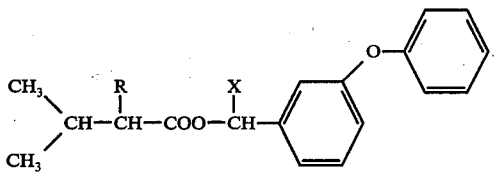

wherein R is a straight-chain alkyl group of 1 to 16 carbon atoms and X is a hydrogen atom or an ethynyl group.

2. A compound according to claim 1 wherein R is n-propyl and X is ethynyl.

3. A compound as claimed in claim 1 wherein R is n-propyl and X is hydrogen.

* * * * *